United States Patent
Götzmann et al.

(10) Patent No.: US 7,214,811 B2
(45) Date of Patent: May 8, 2007

(54) DERIVATIVE OF PHOSPHORIC ACID ESTER SALT OR PHOSPHORIC ACID ESTER ADDUCT OR MIXTURES THEREOF, METHOD FOR THE PRODUCTION THEREOF AND THEIR USE

(75) Inventors: Karl Götzmann, Budenheim (DE); Thomas Futterer, Wiesbaden (DE); Hans-Dieter Nägerl, Dudenhofen (DE); Vincent Mans, Badalona (ES)

(73) Assignee: Chemische Fabrik Budenheim KG, Budenheim (DE)

( * ) Notice: Subject to any disclaimer, the term of this patent is extended or adjusted under 35 U.S.C. 154(b) by 327 days.

(21) Appl. No.: 10/471,644

(22) PCT Filed: Feb. 28, 2002

(86) PCT No.: PCT/DE02/00753

§ 371 (c)(1),
(2), (4) Date: Mar. 1, 2004

(87) PCT Pub. No.: WO02/072590

PCT Pub. Date: Sep. 19, 2002

(65) Prior Publication Data

US 2004/0138477 A1 Jul. 15, 2004

(30) Foreign Application Priority Data

Mar. 14, 2001 (DE) ................. 101 12 155

(51) Int. Cl.
*C07F 9/02* (2006.01)
(52) U.S. Cl. ............... 558/114; 558/113; 558/70; 558/87; 558/89
(58) Field of Classification Search ........... 558/114, 558/113, 70, 87, 89
See application file for complete search history.

(56) References Cited

U.S. PATENT DOCUMENTS 3,651,169 A * 3/1972 Davis, Jr. ............ 525/511

FOREIGN PATENT DOCUMENTS

| AT | 400570 B | 1/1996 |
|---|---|---|
| DE | 4133753 | 4/1993 |
| DE | 4219711 | 12/1993 |
| DE | 19540861 | 5/1997 |
| DE | 19744426 | 7/1999 |
| DE | 19827845 | 12/1999 |
| DE | 19951385 | 5/2001 |
| EP | 0116846 A1 | 8/1984 |
| EP | 0116846 B | 8/1984 |
| EP | 0658561 | 6/1995 |
| EP | 0919591 A | 6/1999 |
| WO | WO 85/05626 | 12/1985 |
| WO | WO9305118 A | 3/1993 |
| WO | WO 99/05200 | 2/1999 |

* cited by examiner

*Primary Examiner*—Joseph K. McKane
*Assistant Examiner*—Robert Shiao
(74) *Attorney, Agent, or Firm*—Michael L. Dunn

(57) ABSTRACT

A derivative of phosphoric acid ester salt or adduct or a mixture thereof is obtained from a reaction product, polycondensed with at least one aldehyde, of at least one polyol phosphoric acid ester with at least one organic nitrogen base. The derivative is advantageously used as a flame-inhibiting and/or intumescent treatment in plastic mouldings, on porous carriers or in paint or coating systems. The production of the derivative or a mixture thereof by reacting at least one polyol with phosphorus pentoxide and reacting the polyol phosphoric acid ester obtained in that way with at least one organic nitrogen base forming a phosphoric acid ester salt or adduct, is characterized in that the amount of phosphorus pentoxide required for the esterification operation is suspended in an amount of the ester or ester mixture to be produced, then at a temperature in the range of 20–180° C. the amount of polyol required for the esterification operation and optionally water is added, then the esterification reaction is allowed to take place substantially completely and thereafter the product is obtained and finally the salt or adduct obtained by reaction of that product with the organic nitrogen base is polycondensed with at least one aldehyde.

23 Claims, No Drawings

DERIVATIVE OF PHOSPHORIC ACID ESTER SALT OR PHOSPHORIC ACID ESTER ADDUCT OR MIXTURES THEREOF, METHOD FOR THE PRODUCTION THEREOF AND THEIR USE

This application is a 371 of PCT/DE02/00753 filed on Feb. 28, 2002.

The use of oligomeric phosphoric acid esters as flameproofing agents specifically for polyurethane foams is known from EP-A-0 658 561 and DE-A-195 40 861. DE-A-198 27 845 discloses flameproofed polyester moulding materials which contain reaction products of polyol phosphoric acid ester with at least one organic nitrogen base such as melamine. A process for the production of polyol phosphoric acid esters is known from WO 99/05200. In the past however phosphoric acid esters as flameproofing agents did not acquire major significance as they are complicated and expensive to produce and the phosphoric acid ester salts or adducts known for example from DE-A-198 27 845 involve excessively high solubility in water.

Accordingly the object of the present invention is that of obtaining new compounds which can be used as flameproofing agents, on the basic of phosphoric acid esters, which are as simple as possible to produce and which are substantially less soluble in water than the known phosphoric acid ester derivatives. It is also desirable to obtain such new compounds with better thermal stability.

In accordance with the invention, that object is attained with derivatives of phosphoric acid ester salts or adducts or mixtures thereof, which were obtained from a reaction product of at least one polyol phosphoric acid ester with at least one organic nitrogen base and which are characterised in that said reaction product is polycondensed with at least one aldehyde.

The specified polycondensation operation according to the invention with aldehyde affords a level of solubility in water which is only about one hundredth or less than that of the corresponding non-polycondensed phosphoric acid ester salts or adducts without the known flameproofing properties suffering. In addition the polycondensates according to the invention have enhanced thermal stability and overall the properties acquired have the result that the derivatives according to the invention can advantageously be used as flameproofing agents or intumescent paint and coating systems.

When used as a flameproofing agent in plastic mouldings, especially for polyolefin mouldings, such as in particular for polyethylene and polypropylene, the polycondensates according to the invention can be added in powder form to the molten plastic material and uniformly distributed in the latter, for example in an extruder.

As mentioned, the derivatives according to the invention however can also be added to paint or coating agents in order to impart flame-retardant surface properties to articles of the most widely varying nature.

Finally the derivatives according to the invention can also be polycondensed directly in a porous carrier and rendered insoluble in the pores, such as for example as a flame-retardant application to fibres, in particular plastic fibres.

Production of the polycondensate desirably involves using a $C_1$–$C_4$-monoaldehyde or a $C_2$–$C_4$-dialdehyde, in which respect the simplest mono- and dialdehydes, namely formaldehyde and acetaldehyde as well as glyoxal are particularly preferably used.

The polyol phosphoric acid esters used as starting materials in accordance with the invention can be the oligomeric phosphoric acid esters known from the literature as flameproofing agents, such as for example those which are known from EP-A-0 658 561 and DE-A-195 40 861. The polyols of those phosphoric acid esters used are for example ethane-1,2-diol, propane-1,2- or 1,3-diol, butane-1,2-, 1,3-, 1,4- or 2,3-diol, glycerine, trimethylolmethane, ethane or propane, neopentylglycol, erythritols, pentaerythritol, di- or polypentaerythritols, pentitols such as arabitol and xylitol, hexitols such as manitol or sorbitol, pentositols, dehydroxybenzols, 2,3-dimethylol-1,3-dihydroxybenzol or mixtures thereof. Preferred in that respect are $C_2$–$C_6$-, in particular $C_4$–$C_6$-polyols, in particular pentaerythritol or sorbitol.

The polyol phosphoric acid esters are reacted with at least one organic nitrogen base to form a salt or adduct. The organic nitrogen bases considered are for example polyvinyl amine, polyethylene imine, methylene diamine, melamine, guanidine, methylol melamine or the condensates thereof and the mixtures thereof. Preferably melamine is used as the organic nitrogen base. In the reaction product which is polycondensed according to the invention the molar ratio of nitrogen base to polyol phosphoric acid ester is preferably 2–3 moles of nitrogen base for 1 mole of polyphosphoric acid ester.

In relation to 1 mole of nitrogen base, preferably melamine, the phosphoric acid ester salt or adduct is desirably polycondensed with 0.5–8, preferably 0.5–4, particularly preferably 0.5–2 moles of monoaldehyde or 0.25–4, preferably 0.25–2, particularly preferably 0.25–1 moles of dialdehyde such as glyoxal.

The properties of the flameproofing agents produced can be adapted to the most widely varying purposes of use by virtue of the choice of various variables. They include the choice of the polyols in ester manufacture, the molar ratio of hydroxyl groups of the polyol in relation to the amount used of phosphorus pentoxide in the esterification operation, the ratio of phosphoric acid ester groups to the amount of organic nitrogen base in the operation of forming the salt or adduct and the amount of aldehyde used in the polycondensation operation.

When using intermolecular diols, the result obtained is esters which under normal conditions are still capable of flow while when using higher polyols such as pentaerythritol, the result is esters of bitumen-like consistency which can only be used in the form of concentrated aqueous solutions.

In general the attempt will be made as far as possible to phosphorylate all hydroxyl groups of the polyol and in that respect to use in each case two hydroxyl groups for 1 mole of phosphorus pentoxide. In that respect the endeavour is to achieve a percentage phosphorus content which is as high as possible. Polyol phosphoric acid esters whose phosphorus content is above 20% are particularly advantageous. Because of the phosphorus content in the end product, in the operation of forming the salt or adduct, the procedure will generally be implemented with only 1 mole of melamine for each 2 moles of phosphoric acid ester groups. It was found to be particularly advantageous to provide in the reaction procedure in respect of phosphoric acid ester salt or adduct of 1.5–2.5 moles of $NH_2$-groups in the organic nitrogen base per ester group. Desirably 0.5–2 moles of formaldehyde are used per mole of melamine.

The preferred process for the production of the derivatives or derivative mixtures according to the invention provides that in ester production from polyol with phosphorus pentoxide the required amount of phosphorus pentoxide is suspended in an amount of the ester or ester mixture to be produced and then at a temperature in the range of 20–180°

C. the amount of polyol required for the esterification operation and possibly water is added, then the esterification reaction is left to proceed substantially completely and then the product is obtained. In that case it is possible to operate with stoichiometric or substantially stoichiometric amounts of phosphorus pentoxide, polyol and optionally water, so that in practice only the desired ester or esters is or are produced and there is no need for subsequently separating off excessive starting materials or solvents.

The addition of polyol and optionally water is advantageously effected at a temperature in the range of 20–150° C., the subsequent completion of the esterification reaction is desirably effected for a period of 1–6 hours at at least the temperature of polyol addition. Desirably, in completion of the esterification reaction, the procedure involves heating and stirring until a clear liquid is produced, which indicates that the reaction was completely effected.

When the reaction is concluded the freshly produced amount of phosphoric acid ester or mixture is removed from the reaction vessel. Thereupon it is possible to begin a new implementation of the reaction, with the residual amount of phosphoric acid ester which has remained in the reaction vessel, by again adding phosphorus pentoxide and suspending it in the finished ester or ester mixture.

The polyol phosphoric acid ester obtained in that way is reacted with organic nitrogen base, with the formation of salts or adducts. That reaction can be carried out separately from ester formation with the separated-off esters or however in the same reaction vessel as the ester formation operation.

Then, the polycondensation operation is effected by the addition of at least the stoichiometric amount of aldehyde such as in particular formaldehyde. The temperature of the polycondensation operation is desirably in the range of 50–100° C. The solid polycondensate which is formed due to its poor solubility in water is then filtered off and used in the form of a powder as a flameproofing agent.

When fibres or other porous carrier materials are to be impregnated with the flameproofing agent, it is desirable to impregnate the fibres or other porous articles with an aqueous solution of the phosphoric acid ester salt or adduct and then to treat the impregnated fibres with the aldehyde, in which case the desired polycondensate is formed in the pores of the fibres or of the other porous carrier.

EXAMPLE 500g of pentaerythritetetraorthophosphoric acid monoester is put in a round-bottomed flask with a useful capacity of 1l and equipped with an agitator, thermometer, reflux condenser and dropping funnel. Because of the viscosity of that substance the procedure involves first heating with agitation to a temperature of 80–90° C. When that temperature is reached 142 g of phosphorus pentoxide is added and suspended with agitation. A pasty mixture of 68 g of pentaerythrite and 18 g of water is then introduced in portion-wise manner. When everything has been added, the temperature is increased to 150° C. and agitation is continued at that temperature until a clear liquid is produced. After cooling to about 80° C. the resulting amount of pentaerythritetetraphosphoric acid monoester (228 g) is removed.

Introduced with agitation into a melamine suspension heated to 80° C. is as much of the above-produced 80% aqueous ester solution, as corresponds to the desired molar ratio of 1 mole of ester per 3 moles of melamine. A perceptible reaction takes place immediately, which is revealed by a substantial increase in viscosity. After some minutes the viscosity falls again, whereby salt formation is concluded.

The salt formed is then polycondensed with formaldehyde. It was found to be desirable to use 0.5–8 moles of formaldehyde per mole of melamine, preferably 0.5–4 moles of formaldehyde per mole of melamine and particularly preferably 0.5–2 moles of formaldehyde per mole of melamine, for the polycondensation operation.

The addition of formaldehyde is effected in the form of a commercially available 37% solution. After the addition operation the solid suspension is agitated for a further 30 minutes at 80° C. and thereafter the solid material is separated off with a suitable filter. The filter residue is subsequently washed with water and then dried. The filtrate and the washing water are combined and used in a next implementation of the procedure as suspension media for the melamine.

The flameproofing agent according to the invention formed in that way had the following properties:

| | |
|---|---|
| Nature: | pure powder |
| P-content: | about 23% |
| N-content: | about 27% |
| pH-value (1%): | about 3.6 |
| Apparent density: | g/l about 700 |
| Decomposition temperature: | about 310° C. |
| Intumescence: | great |
| Water solubility: | at 20° C. <0.02 g/100 ml water |
| | at 80° C. <0.05 g/100 ml water |

The invention claimed is:

1. A derivative of phosphoric acid ester salt or adduct or mixtures thereof obtained by reaction of at least one polyol phosphoric acid ester with at least one organic nitrogen base to obtain the salt or adduct reaction product and polycondensing the reaction product with at least one aldehyde to obtain the derivative.

2. A derivative according to claim 1 wherein the reaction product is polycondensed with a $C_1$–$C_4$-monoaldehyde or a $C_2$–$C_4$-dialdehyde.

3. A derivative according to claim 1 wherein the reaction product is condensed with formaldehyde, acetylaldehyde or glyoxal.

4. A derivative according to claim 1 wherein the reaction product is polycondensed with from 0.5 to 8 moles of monoaldehyde per mole of organic nitrogen base.

5. A derivative according to claim 1 wherein the reaction product is polycondensed with from 0.5 to 4 moles of monoaldehyde per mole of organic nitrogen base.

6. A derivative according to claim 1 wherein the reaction product is polycondensed with 0.25 to 4 moles of dialdehyde per mole of organic nitrogen base.

7. A derivative according to claim 1 wherein the reaction product is polycondensed with 0.25 to 2 moles of dialdehyde per mole of organic nitrogen base.

8. A derivative according to claim 1 wherein the reaction product is obtained by reaction of 2 to 3 moles of organic nitrogen base per mole of polyol phosphoric acid ester.

9. A derivative according to claim 1 wherein the reaction product is obtained using melamine, guanidine or ethylene diamine as the nitrogen base.

10. A derivative according to claim 2 wherein the reaction product is obtained using melamine, guanidine or ethylene diamine as the nitrogen base.

11. A derivative according to claim 3 wherein the reaction product is obtained using melamine, guanidine or ethylene diamine as the nitrogen base.

12. A derivative according to claim 1 wherein the polyol phosphoric acid ester is a $C_4$–$C_6$-polyol phosphoric acid ester.

13. A derivative according to claim 1 wherein the polyol phosphoric acid ester is pentaerythritol or sorbitol.

14. A process for the preparation of a derivative of phosphoric acid ester salt, or adduct or a mixture thereof according to claim 1 by reacting at least one polyol with phosphorus pentoxide and reacting the resulting polyol phosphoric acid ester with at least one organic nitrogen base forming a phosphoric acid ester salt or adduct, wherein an amount of phosphorus pentoxide, or phosphorus pentoxide and water, required for esterification is suspended in the ester or ester mixture of the type to be produced, then at a temperature in the range of 20–180° C. an amount of polyol required for the esterification is added, and then the esterification reaction is allowed to take place substantially completely to obtain the phosphoric acid ester which is then reacted with the organic nitrogen base to obtain the salt or adduct which is then polycondensed with at least one aldehyde to obtain the desired derivative.

15. A process according to claim 14 wherein substantially stoichiometric amounts of phosphorus pentoxide, or phosphorus pentoxide and water, and polyol are added.

16. A process according to claim 14 wherein polyol or phosphorus pentoxide and water, are added at a temperature in the range of 20–150° C.

17. A process according to claim 15 wherein polyol, or phosphorus pentoxide and water, are added at a temperature in the range of 20–150° C.

18. A process according to claim 14 wherein the esterification reaction is completed at at least the temperature of addition of polyol, or phosphorus pentoxide and water, during a period of 1–6 hours.

19. A process according to claim 15 wherein the esterification reaction is completed at at least the temperature of addition of polyol and optionally water during a period of 1–6 hours.

20. A process according to claim 16 wherein the esterification reaction is completed at at least temperature of addition of polyol and optionally water during a period of 1–6 hours.

21. A method for flame inhibition comprising incorporating a derivative prepared according to claim 1 as a flame-inhibiting treatment in plastic moulding, on porous carriers or in paint or coating systems.

22. A method for intumescent treatment comprising incorporating a derivative prepared according to claim 1 in plastic moulding, or porous carriers or in paints or coating systems.

23. The method of claim 21 as a flameproofing method for polyolefins.

* * * * *